United States Patent
Hubbard et al.

(10) Patent No.: US 6,746,416 B2
(45) Date of Patent: Jun. 8, 2004

(54) DUPLEX BLOOD PUMP FOR HEART SURGERY

(75) Inventors: Lloyd Hubbard, Deephaven, MN (US); Earl Clausen, Newport, MN (US)

(73) Assignee: Spin Corporation, Deephaven, MN (US)

( * ) Notice: Subject to any disclaimer, the term of this patent is extended or adjusted under 35 U.S.C. 154(b) by 426 days.

(21) Appl. No.: 10/016,356

(22) Filed: Dec. 5, 2001

(65) Prior Publication Data

US 2003/0105420 A1 Jun. 5, 2003

(51) Int. Cl.[7] ............... A61M 37/00; F04B 49/00
(52) U.S. Cl. ............... 604/6.11; 604/6.14; 417/294; 415/900
(58) Field of Search ............... 422/44–48; 604/4.01, 604/6.01, 6.14, 6.11, 6.16, 7–9, 93.01, 131, 151, 154–55, 264, 523, 532–33, 538; 417/321, 375, 405, 406, 409, 410.1, 420, 572, 902; 415/13, 25, 182.1, 203, 229–30, 231, 900, 4

(56) References Cited

U.S. PATENT DOCUMENTS

| | | |
|---|---|---|
| 4,589,822 A | 5/1986 | Clausen et al. .......... 415/170 A |
| 4,606,698 A | 8/1986 | Clausen et al. .......... 415/170 A |
| 4,693,714 A | 9/1987 | Lundback .................... 623/3 |
| 4,756,705 A | 7/1988 | Beijbom et al. ............... 604/4 |
| 4,778,445 A | 10/1988 | Hubbard et al. ............... 604/4 |
| 4,781,525 A | 11/1988 | Hubbard et al. ............. 415/30 |
| 4,781,716 A | 11/1988 | Richelsoph .................... 623/3 |
| 4,820,300 A | 4/1989 | Pierce et al. .................. 623/3 |
| 4,898,518 A | 2/1990 | Hubbard et al. ........... 417/360 |
| 4,936,759 A | 6/1990 | Clausen et al. ......... 417/423.14 |
| 4,984,972 A | 1/1991 | Clausen et al. ............ 417/420 |
| 5,066,300 A | 11/1991 | Isaacson et al. ............. 623/3 |
| 5,360,317 A | 11/1994 | Clausen et al. ............ 415/206 |
| 5,411,706 A | 5/1995 | Hubbard et al. ............. 422/46 |
| 5,458,459 A | 10/1995 | Hubbard et al. ........... 415/206 |
| 5,676,651 A | 10/1997 | Larson, Jr. et al. .......... 604/33 |
| 5,743,845 A | 4/1998 | Runge ........................ 600/16 |
| 5,807,737 A | 9/1998 | Schill et al. ............. 435/284.1 |
| 5,851,174 A | 12/1998 | Jarvik et al. ................ 600/16 |
| 5,965,089 A | 10/1999 | Jarvik et al. ................ 422/44 |
| 6,048,363 A | 4/2000 | Nagyszalanczy et al. ...... 623/3 |
| 6,139,487 A | 10/2000 | Siess ........................ 600/16 |

*Primary Examiner*—Patricia Bianco
(74) *Attorney, Agent, or Firm*—Kinney & Lange, P.A.

(57) ABSTRACT

A two-chambered centrifugal blood pump for pumping biological fluids such as blood. One chamber is for pumping blood through the natural lungs, and a second chamber is for pumping blood through the remainder of the body. Each chamber has it's own inlet and outlet ports for attachment of tubing and cannulae. A small, adjustable clamp may alternatively be provided if minor adjustments of pressure to both the pulmonary and systemic circuits is required.

27 Claims, 3 Drawing Sheets

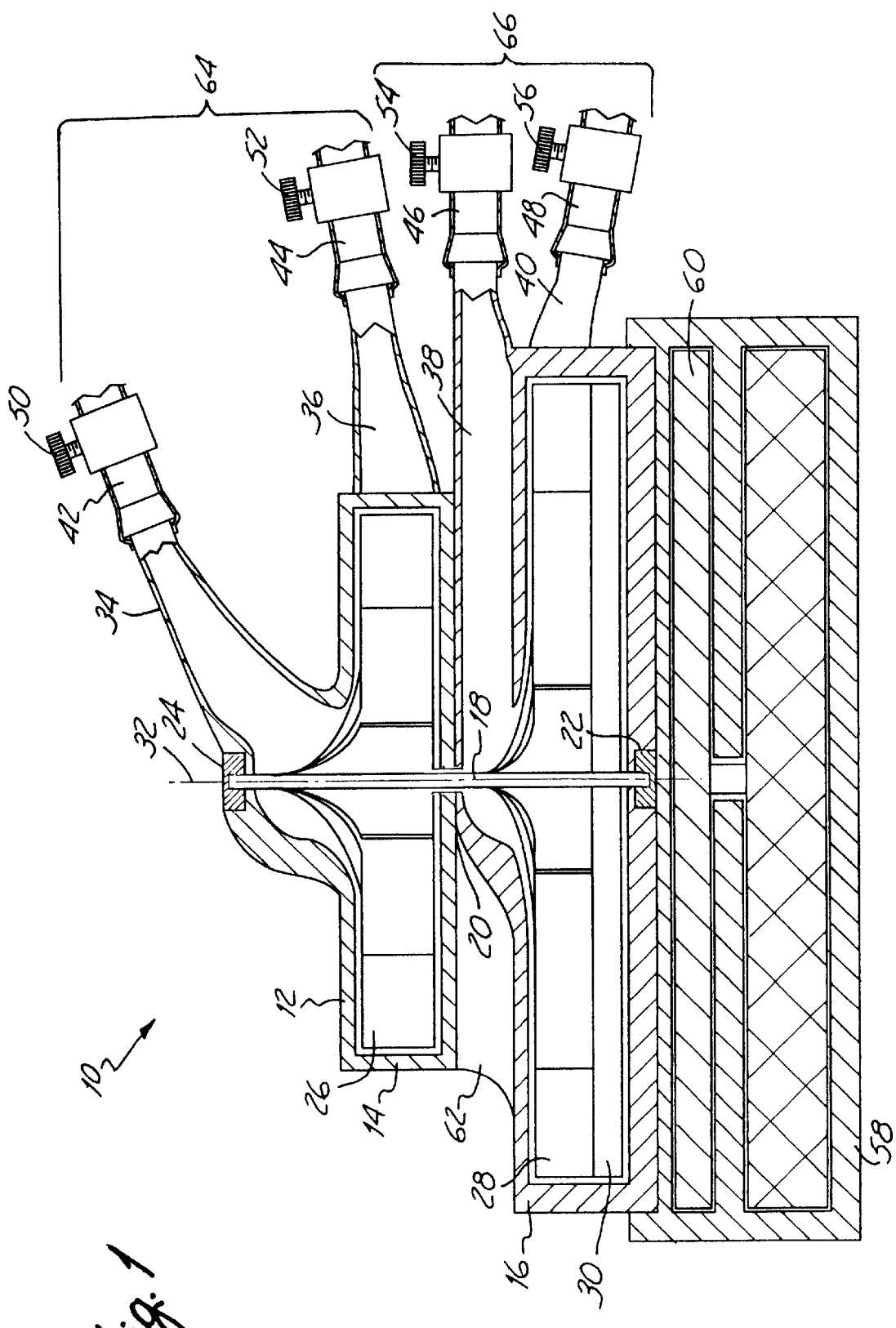

DUPLEX BLOOD PUMP FOR HEART SURGERY

CROSS-REFERENCE TO RELATED APPLICATION(S)

None.

BACKGROUND OF THE INVENTION

The present invention relates to centrifugal blood pumps.

Delicate surgical procedures require that the site of surgery remain motionless. This requirement made early heart surgery difficult to impossible as interruption of the heart's pumping action for the required length of surgical time would invariably be fatal.

Traditional heart surgery is carried out with the aid of devices generally referred to as a "heart/lung machine". With the heart/lung machine in operation, the patient's heart can be stopped while the surgeon performs the delicate surgery required to repair the ailing heart. The two fundamental parts of the heart/lung machine are a blood pump that takes the place of the arrested heart, and an oxygenator that replaces the patient's lungs during the surgical procedure. The heart/lung machine also includes filters, blood reservoirs, and plastic tubing as required to connect several parts of the bypass circuit.

Although the mortality and morbidity of heart/lung bypass surgery have been greatly reduced, hospital stays of two weeks and a gradual recovery of over six months are the norm. Many of the bad side-effects of heart/lung surgery are thought to be the result of blood contact with the various parts of the heart/lung machine.

Quite recently, a new technique for heart surgery has been developed. The technique is generally referred to as "surgery on the beating heart". In this process, a stabilizing device is used to hold steady the portion of the heart that is being addressed by the surgeon. The heart/lung machine is not required, because the heart and lungs function normally throughout the procedure. Advantages claimed for this method include reduced hospital stay, reduced hospital cost, and fewer side-effects such as mental deficit. All of these advantages are claimed due to the reduced blood trauma by elimination of blood contact with the devices making up the heart/lung machine.

Beating-heart surgery is not without some problems both for the surgeon and the patient. First, the most commonly used stabilizing device consists in part of a series of small suction cups that attach to the portion of the heart being stabilized. The relatively high vacuum required to grasp the heart typically results in blood blisters on the heart muscle at the site of the suction cups. Second, since the heart is pumping, the surgeon must contend with blood spurting from the coronary artery during graft attachment. Third, there is no data concerning the durability of the coronary artery graft done with this procedure. Lastly, the cost of disposable devices is comparable to that required for conventional open-heart surgery.

The single component of the heart/lung machine that is most suspect for blood trauma is the oxygenator. This is typically a device with hundreds of hollow plastic fibers. The blood passes over the outside surface of the fibers and oxygen passes through the fibers to imitate the function of the natural lungs. Unlike the natural lungs, however, the hollow fibers are made out of a plastic material and must have a large surface area in order to oxygenate the blood and remove carbon dioxide from it. Elimination of the oxygenator would also eliminate tubing, reservoirs, and filters resulting in a significant reduction of foreign blood-contact surfaces.

The mammalian heart performs two pumping functions. The first function is to pump blood through the lungs, and the second is to pump blood to the remainder of the body. The elimination of the oxygenator can be accomplished through the use of two mechanical blood pumps to duplicate the function of the natural heart. This method has been tried experimentally but has not gained favor because of several problems. First, the use of two blood pumps requires that they be synchronized. This is technically difficult with roller-type pumps, which are the most commonly used type in open-heart surgery. Second, cannulae must be placed in both the systemic and pulmonary circuits, which increases surgical time. Third, the extra cannulae crowd the operating area and compromise ready access to the heart. Fourth, although conventional centrifugal blood pumps readily self-synchronize, their size adds to the crowding of the operating field.

BRIEF SUMMARY OF THE INVENTION

With the present invention, the reduction of blood trauma is achieved by eliminating the oxygenator. The present device is a two-chambered centrifugal blood pump. The first chamber has a first inlet and a first outlet and the second chamber has a second inlet and a second outlet. A shaft extends through and between the first and second chambers and defines a rotational axis. First and second impellers are also positioned within the first and second pumping chambers, respectively. In the preferred embodiment, one chamber pumps deoxygenated blood to the natural lungs, and the other chamber pumps oxygenated blood to the remainder of the body.

BRIEF DESCRIPTION OF THE DRAWINGS

FIG. 1 is a cross-sectional view of the preferred embodiment of the invention.

FIG. 2a is a cross-sectional view of the duplex pump including a shaft seal.

DETAILED DESCRIPTION

Figure 6A:
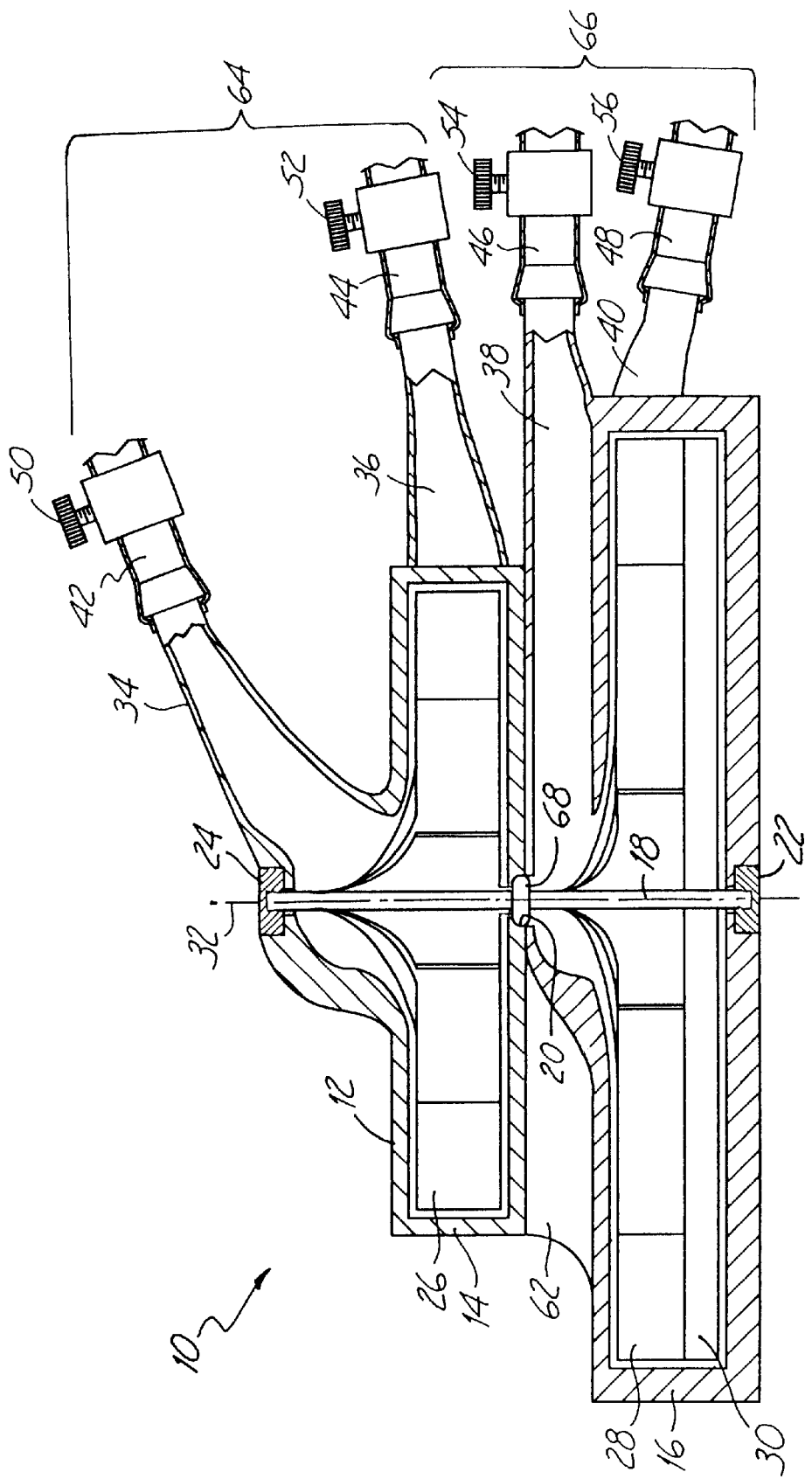

FIG. 1 shows the preferred embodiment of the present invention. Duplex pump 10 includes housing 12, first pumping chamber 14, second pumping chamber 16, shaft 18, opening 20, back bearing 22, front bearing 24, first impeller 26, second impeller 28 with magnets 30, axis of rotation 32, first inlet 34, first outlet 36, second inlet 38, second outlet 40, first and second pulmonary flow lines 42 and 44, first and second systemic flow lines 46 and 48, clamps 50, 52, 54, and 56, drive motor 58 with magnets 60, web 62, pulmonary unit 64, and systemic unit 66.

Housing 12 forms first chamber 14 and second chamber 16, with first chamber 14 positioned on top of second chamber 16. Shaft 18 extends from second chamber 16 through opening 20 to first chamber 14 and is supported by back bearing 22 and front bearing 24. First impeller 26 is positioned within first chamber 14 and connected to shaft 18. Second impeller 28 with magnets 30 is positioned within second chamber 16 and connected to shaft 18. Shaft 18 with impellers 26 and 28 rotate about axis of rotation 32. First inlet 34 and first outlet 36 extend from first chamber 14, and second inlet 38 and second outlet 40 extend from second chamber 16. Flow lines 42, 44, 46, and 48 are coupled to first inlet 34, first outlet 36, second inlet 38, and second outlet 40, respectively. Clamps 50, 52, 54, and 56 are adjustably attached to flow lines 42, 44, 46, and 48, respectively. Drive motor 58 contains magnets 60, which are magnetically coupled to magnets 30 in impeller 28. Web 62 aids in support of first chamber 14 over second chamber 16. Collectively, first chamber 14, shaft 18, impeller 26, first inlet 34, first outlet 36, and flow lines 42 and 44 form pulmonary unit 64. Accordingly, second chamber 16, shaft 18, impeller 28, second inlet 38, second outlet 40, and flow lines 46 and 48 form systemic unit 66.

To power duplex pump 10, drive motor 58 rotates magnets 60 around axis of rotation 32. Magnets 60 are magnetically coupled to magnets 30 in second impeller 28. Thus, second impeller 28, shaft 18, and first impeller 26 synchronously rotate around axis of rotation 32. First impeller 26 and second impeller 28 are preferably a bladed-type impeller, but any other type of impeller or device which provides the proper fluid motion can be used.

In operation, liquid is pumped through a load having two circuits, or preferably, blood is pumped through the pulmonary and systemic circuits of a patient. Flow line 42 connects to a source of systemic venous blood such as the right atrium or vena cava, and flow line 44 connects to a pulmonary artery of the patient. Flow line 46 connects to a source of oxygenated blood such as the left atrium or left ventricle, and flow line 48 connects to a systemic artery of the patient, such as the aorta. Deoxygenated blood from the right atrium or vena cava enters first chamber 14 through first inlet 34. The blood contacts first impeller 26, and is propelled to and through first outlet 36 and to a pulmonary artery. Thus, pulmonary unit 64 performs the function of carrying deoxygenated blood from the patient's systemic circuit to the patient's lung or lungs to become oxygenated.

Simultaneously, oxygenated blood from the left atrium or left ventricle enters second chamber 16 through second inlet 38. The blood contacts second impeller 28, and is propelled to and through second outlet 40 and to the aorta. Systemic unit 66, thus, performs the function of dispersing oxygenated blood from the patient's pulmonary circuit to the patient's systemic circuit.

Alternatively, clamps 50, 52, 54, and 56 may be attached to flow lines 42, 44, 46, and 48, respectively. Clamps 50, 52, 54, and 56 may be adjusted, as needed, to make minor adjustments in pressure to either of the circuits.

In the preferred embodiment, opening 20 remains open which allows some leakage between first chamber 14 and second chamber 16. In this embodiment, the blood remains in motion and is less likely to form clots. However, a seal may fitted within opening 20 to prevent any leakage. Two variations of sealing off first chamber 14 and second chamber 16 are presented in FIGS. 2a and 2b.

FIG. 2a shows duplex pump 10 with shaft 18 supported by back bearing 22 and front bearing 24. Shaft seal 68 is fitted circumferentially around shaft 18 within opening 20. Shaft seal 68 may be an o-ring or the like.

Figure 2B:
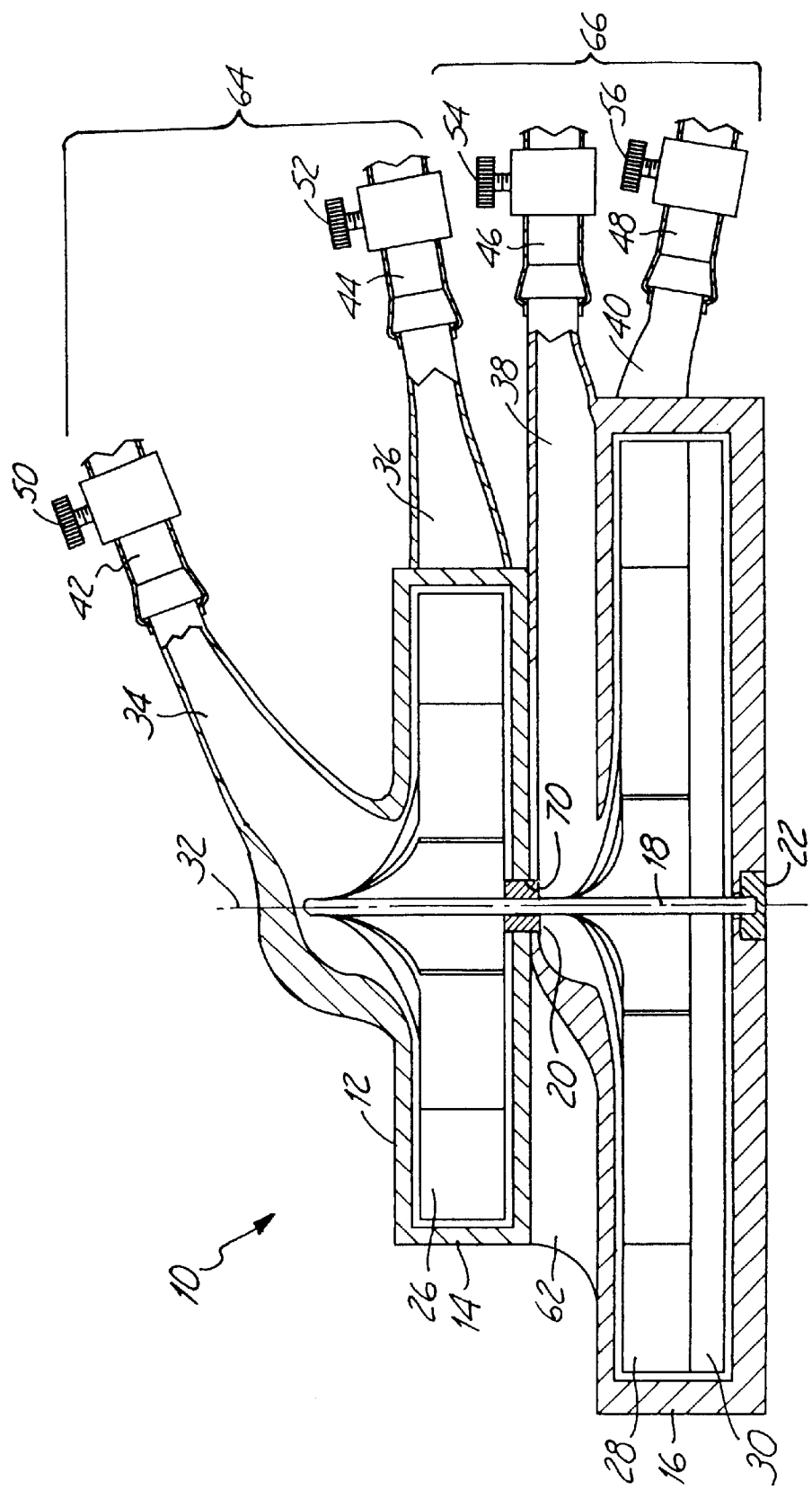
FIG. 2b is a cross-sectional view of the duplex pump including a shaft bearing.

FIG. 2b shows duplex pump 10 with shaft 18, which is supported by back bearing 22 and shaft bearing 70. Shaft bearing 70 is fitted into opening 20 and circumferentially around shaft 18. In this embodiment, front bearing 24 is not necessary because shaft 18 is supported by shaft bearing 70.

There are several advantages of using the present invention for heart/lung bypass. First, many of the benefits of beating-heart surgery is attained but with the surgical advantages of conventional heart/lung bypass surgery. Second, systemic unit 66 is much smaller than conventional centrifugal blood pumps, because there is no need to overcome the pressure resistance of the traditional heart/lung machine. Pulmonary unit 64 is even smaller because of the lower resistance of the pulmonary circuit. The small size of units 64 and 66 allow pump 10 to be placed close to the operating field, which reduces the length of tubing normally required by a heart/lung machine. Third, the reduced pressure requirement also permits using smaller diameter tubing and cannulae, which further reduces clutter at the operating field. Fourth, no special equipment or controls are required to equalize the flow between the pulmonary and systemic circuits, because centrifugal pumps are inherently self-balancing. Fifth, eliminating an oxygenator, and eliminating or reducing other disposable products used in conventional open-heart surgery reduces the cost of the procedure.

Although the present invention has been described with reference to preferred embodiments, workers skilled in the art will recognize that changes may be made in form and detail without departing from the spirit and scope of the invention.

What is claimed is:

1. A centrifugal pump for pumping biological fluids such as blood, the pump comprising:
    a housing defining first and second pumping chambers, the first pumping chamber in fluid communication with the second pumping chamber;
    a first inlet and first outlet in communication with the first pumping chamber;
    a second inlet and second outlet in communication with the second pumping chamber;
    a shaft extending in an axial direction in the housing for defining a rotational axis;
    a first impeller positioned in the first pumping chamber; and
    a second impeller positioned in the second pumping chamber.

2. The pump of claim 1 and further comprising:
    a seal between the first and second pumping chambers, which fits circumferentially around the shaft and prevents leakage between the first and second chambers.

3. The pump of claim 2 wherein the seal is an o-ring.

4. The pump of claim 2 wherein the seal is a bearing.

5. The pump of claim 1 and further comprising:
    a pump drive motor coupler, wherein the coupler is attached to the shaft; and
    a pump drive motor.

6. The pump of claim 1 wherein the pump drive motor coupler is a magnetic coupler.

7. The pump of claim 1 wherein the first pumping chamber is positioned on top of the second pumping chamber.

8. The pump of claim 1 wherein the first and second impellers are attached to the shaft.

9. The pump of claim 1 and further comprising:
    flow lines attached to the first and second inlets and the first and second outlets.

10. The pump of claim 1 and further comprising:
    clamps attached to each flow line for adjusting pressure.

11. The pump of claim 1 wherein the first pumping chamber pumps blood through a pulmonary circuit of a patient.

12. The pump of claim 1 wherein the second pumping chamber pumps blood through a systemic circuit of a patient.

13. A heart/lung apparatus for connection to a patient during heart surgery, the apparatus comprising:
- a centrifugal pump having a housing, first and second pumping chambers, first and second inlets, first and second outlets, first and second impellers, and a shaft;
- a first pulmonary flow line for connection to the first inlet and a source of systemic venous blood;
- a second pulmonary flow line for connection to the first outlet and a pulmonary artery;
- a first systemic flow line for connection to the second inlet and a source of oxygenated blood; and
- a second systemic flow line for connection to the second outlet and a systemic artery.

14. The apparatus of claim 13 wherein the first and second pumping chambers are in fluid communication, and the shaft extends between and through the first and second pumping chambers.

15. The apparatus of claim 14 and further comprising:
- a seal between the first and second pumping chambers, which fits circumferentially around the shaft and prevents leakage between the first and second pumping chambers.

16. The apparatus of claim 15 wherein the seal is an o-ring.

17. The apparatus of claim 15 wherein the seal is a bearing.

18. The apparatus of claim 13 and further comprising:
- a pump drive motor; and
- a pump drive coupler connected to the shaft.

19. The apparatus of claim 18 wherein the pump drive coupler is a magnetic coupler.

20. The apparatus of claim 13 wherein the shaft extends in an axial direction between and through the first and second chambers, and the first and second impellers are coupled to the shaft.

21. The apparatus of claim 20 wherein the first and second impellers and shaft rotate in a synchronized fashion.

22. The apparatus of claim 13 and further comprising:
- clamps adjustably connected to each flow line.

23. A pumping apparatus for pumping liquids to a load, the apparatus comprising:
- a centrifugal pump containing first and second chambers positioned such that the first chamber is on top of the second chamber, an opening between the first and second chambers with a shaft extending from the first chamber through the opening and into the second chamber, a first impeller within the first chamber and connected to the shaft, a second impeller within the second chamber and connected to the shaft, a first inlet and first outlet in communication with the first chamber, a second inlet and second outlet in communication with the second chamber, flow lines coupling each inlet and outlet with the load; and
- a pump drive motor magnetically coupled to the second impeller to provide a source of rotation.

24. The apparatus of claim 23 and further comprising:
clamps connected to each flow line to adjust pressure.

25. The apparatus of claim 23 and further comprising:
- a seal fitted between the first and second chambers and circumferentially around the shaft, which prevents any fluid leakage between the first and second chambers.

26. A centrifugal pump for pumping biological fluids, adapted to be coupled to an external source of rotation, comprising:
- a first chamber, having a first inlet and first outlet, for pumping fluids through a pulmonary circuit of a patient;
- a second chamber, having a second inlet and second outlet, for pumping fluids through a systemic circuit of a patient, the second chamber being fluidly coupled to the first chamber;
- a shaft which extends through and is enclosed by the first and second chambers for rotation about an axis of rotation;
- a first impeller enclosed in the first chamber and being supported on the shaft;
- a second impeller enclosed in the second chamber and being supported on the shaft in a spaced relationship to the external source of rotation, the second impeller coupled with the external source of rotation for rotating the impeller about the axis of rotation; and
- wherein the first impeller rotates about the axis of rotation by way of the rotation of the second impeller.

27. The pump of claim 26 wherein the coupling means comprises:
- magnetic means carried by the second impeller for magnetically coupling to the external source of rotation.

* * * * *